US012361539B2

(12) United States Patent
Cheng et al.

(10) Patent No.: US 12,361,539 B2
(45) Date of Patent: Jul. 15, 2025

(54) CLASSIFICATION METHOD AND CLASSIFICATION DEVICE FOR CLASSIFYING LEVEL OF AMD

(71) Applicant: Acer Medical Inc., New Taipei (TW)

(72) Inventors: Meng-Che Cheng, New Taipei (TW); Ming-Tzuo Yin, New Taipei (TW); Yi-Ting Hsieh, Taipei (TW)

(73) Assignee: Acer Medical Inc., New Taipei (TW)

( * ) Notice: Subject to any disclaimer, the term of this patent is extended or adjusted under 35 U.S.C. 154(b) by 554 days.

(21) Appl. No.: 17/462,020

(22) Filed: Aug. 31, 2021

(65) Prior Publication Data

US 2022/0366559 A1 Nov. 17, 2022

(30) Foreign Application Priority Data

May 14, 2021 (TW) .................................. 110117544

(51) Int. Cl.
*A61B 3/12* (2006.01)
*A61B 5/00* (2006.01)
(Continued)

(52) U.S. Cl.
CPC .............. *G06T 7/0012* (2013.01); *A61B 3/12* (2013.01); *A61B 5/7267* (2013.01);
(Continued)

(58) Field of Classification Search
CPC ......... G06T 7/0012; G06T 2207/20084; G06T 2207/30041; G06V 40/193; G06V 40/197; G16H 30/40; G16H 50/20
See application file for complete search history.

(56) References Cited

U.S. PATENT DOCUMENTS

2014/0126787 A1* 5/2014 Zuhlke Kimball ....... G06T 7/68
382/128
2017/0142384 A1* 5/2017 Yoshimura ........... H04N 9/3185
(Continued)

FOREIGN PATENT DOCUMENTS

CN 112508864 3/2021
TW 202038137 10/2020
WO 2014074178 5/2014

OTHER PUBLICATIONS

Govindahiah, "Deep Convolutional neural network based screening and assessment of age-related Macular Degeneration from Fundus Image", Apr. 2018, IEEE 15th international Symposium on Biomedical Imaging, pp. 1525-1528. (Year: 2018).*

(Continued)

*Primary Examiner* — Jeanette J Parker
(74) *Attorney, Agent, or Firm* — JCIPRNET

(57) ABSTRACT

A classification method and a classification device for classifying a level of an age-related macular degeneration are provided. The classification method includes the following. An object detection model and a first classification model are pre-stored. A fundus image is obtained. A bounding box is generated in the fundus image according to a macula in the fundus image detected by the object detection model. An intersection over union between a predetermined area and the bounding box in the fundus image is calculated. A classification of the fundus image is generated according to the first classification model in response to the intersection over union being greater than a threshold.

4 Claims, 4 Drawing Sheets

(51) Int. Cl.
  *G06T 7/00* (2017.01)
  *G06V 40/18* (2022.01)
  *G16H 30/40* (2018.01)
  *G16H 50/20* (2018.01)
(52) U.S. Cl.
  CPC .......... *G06V 40/193* (2022.01); *G06V 40/197* (2022.01); *G16H 30/40* (2018.01); *G16H 50/20* (2018.01); *G06T 2207/20084* (2013.01); *G06T 2207/30041* (2013.01)

(56) References Cited

U.S. PATENT DOCUMENTS

| | | | | |
|---|---|---|---|---|
| 2018/0235467 | A1* | 8/2018 | Celenk | A61B 3/14 |
| 2021/0219839 | A1* | 7/2021 | Kim | G16H 20/40 |
| 2021/0390692 | A1* | 12/2021 | Srivastava | A61B 3/0025 |
| 2022/0175325 | A1* | 6/2022 | Fukushima | A61B 5/7264 |
| 2022/0189009 | A1* | 6/2022 | Wang | G06F 18/24 |
| 2022/0207729 | A1* | 6/2022 | Boyd | G06V 40/193 |
| 2023/0037424 | A1* | 2/2023 | Elen | G06V 40/18 |

OTHER PUBLICATIONS

Jyoti Prakash Medhi et al., "Automatic Grading of Macular Degeneration from Color Fundus Images.", 2012 World Congress on Information and Communication Technologies. IEEE. Oct. 30, 2012, with English abstract, pp. 511-514.

Cheung Ronald et al., "Diagnostic accuracy of current machine learning classifiers for age-related macular degeneration: a systematic review and meta-analysis.", retrieved on Mar. 4, 2022, available at http://www.nature.com/articles/s41433-021-01540-y.pdf.

MHD Hasan Sarhan et al. "Machine Learning Techniques for Ophthalmic Data Processing: A Review.", IEEE Journal of Biomedical and Health Informatics, vol. 24, No. 12, Dec. 3, 2020, with English abstract, pp. 3338-3350.

"Search Report of Europe Counterpart Application", issued on Mar. 15, 2022, with English abstract, pp. 1-11.

* cited by examiner

CLASSIFICATION METHOD AND CLASSIFICATION DEVICE FOR CLASSIFYING LEVEL OF AMD

CROSS-REFERENCE TO RELATED APPLICATION

This application claims the priority benefit of Taiwanese application no. 110117544, filed on May 14, 2021. The entirety of the above-mentioned patent application is hereby incorporated by reference herein and made a part of this specification.

BACKGROUND

Technical Field

The disclosure relates to a classification method and a classification device for classifying a level of age-related macular degeneration.

Description of Related Art

When determining a level of age-related macular degeneration (AMD) with an artificial intelligence (AI) model, input data of the artificial intelligence model includes mostly original fundus images or pre-processed fundus images. However, when determining severity level of the AMD, a doctor does not base a diagnosis on an entire eyeball area in a fundus image, but on a macula in the fundus image. In other words, the artificial intelligence model and the doctor have different determination criteria. Therefore, the determination result of the artificial intelligence model may be inaccurate.

SUMMARY

The disclosure provides a classification method and a classification device for classifying a level of age-related macular degeneration, in which the level of AMD can be classified according to a reasonable area in a fundus image.

In the disclosure, a classification device for classifying a level of age-related macular degeneration includes a processor, a storage medium, and a transceiver. The storage medium stores an object detection model and a first classification model. The processor is coupled to the storage medium and the transceiver. The processor is configured to obtain a fundus image through the transceiver, generate a bounding box in the fundus image according to a macula in the fundus image detected by the object detection model, calculate an intersection over union between a predetermined area and the bounding box in the fundus image, and generate a classification of the fundus image according to the first classification model in response to the intersection over union being greater than a threshold.

In an embodiment of the disclosure, the storage medium further stores a second classification model. The processor is further configured to generate the classification of the fundus image according to the second classification model in response to the intersection over union being less than or equal to the threshold.

In an embodiment of the disclosure, the processor inputs an image in the bounding box into the first classification model to generate the classification.

In an embodiment of the disclosure, the processor inputs the fundus image into the second classification model to generate the classification.

In an embodiment of the disclosure, a center point of the predetermined area is located at a geometric center of the fundus image.

In an embodiment of the disclosure, the fundus image and the predetermined area are rectangles. A first edge of the predetermined area is distanced from a first boundary of the fundus image by a first distance, and a second edge of the predetermined area is distanced from a second boundary of the fundus image by the first distance. The second edge is an opposite edge of the first edge, and the second boundary is an opposite edge of the first boundary.

In an embodiment of the disclosure, the predetermined area is a rectangle. The processor is further configured to obtain an eyeball area in the fundus image, and generate a length of a long edge and a length of a short edge of the rectangle according to a diameter of the eyeball area.

In an embodiment of the disclosure, the classification indicates correspondence of the fundus image to one of a first stage, a second stage, a third stage, and a fourth stage of the age-related macular degeneration.

In an embodiment of the disclosure, the first classification model and the second classification model have a same convolutional neural network architecture.

In the disclosure, a classification method for classifying a level of age-related macular degeneration includes the following. An object detection model and a first classification model are pre-stored. A fundus image is obtained. A bounding box is generated in the fundus image according to a macula in the fundus image detected by the object detection model. An intersection over union between a predetermined area and the bounding box in the fundus image is calculated. A classification of the fundus image is generated according to the first classification model in response to the intersection over union being greater than a threshold.

Based on the foregoing, the classification device of the disclosure may classify the level of the AMD according to the same determination criteria with the doctor when a position of the macula in the fundus image is reasonable. If the position of the macula in the fundus image is not reasonable, the classification device may classify the level of the AMD according to the entire fundus image.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

Figure 1:
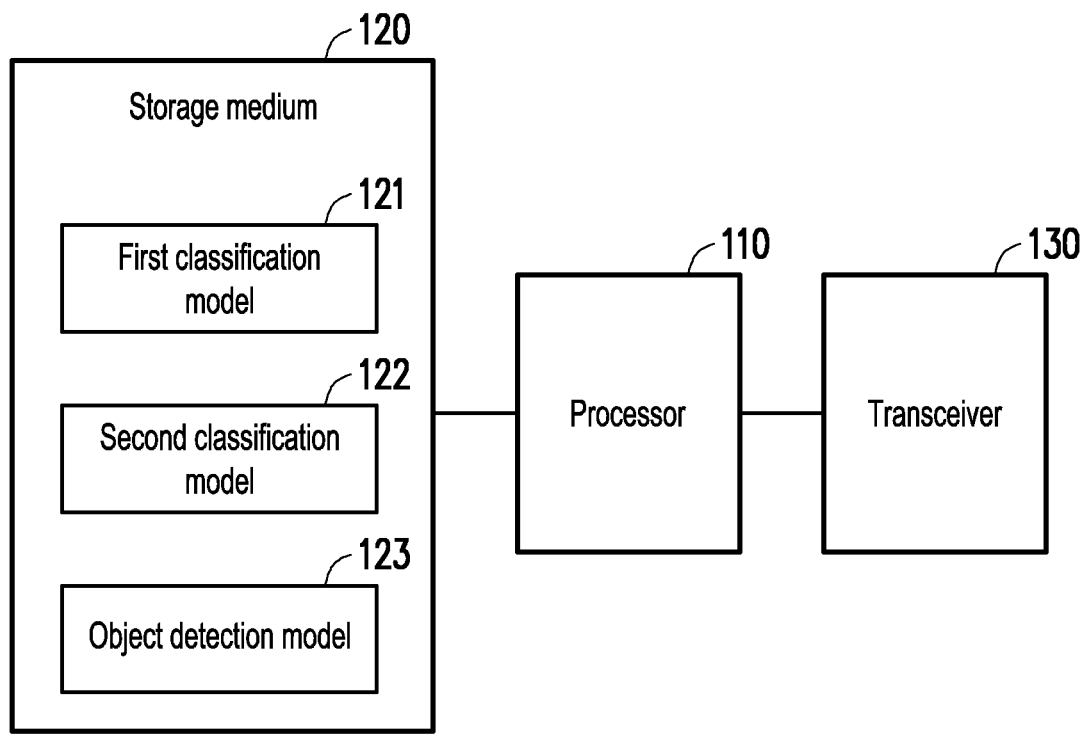
FIG. 1 is a schematic diagram showing a classification device for classifying a level of AMD according to an embodiment of the disclosure.

To make the content of the disclosure more comprehensible, embodiments will be described below as examples for reliably implementing the disclosure accordingly. In addition, wherever possible, elements/members/steps labeled with the same reference numerals in the drawings and embodiments refer to the same or similar parts.

FIG. 1 is a schematic diagram showing a classification device 100 for classifying a level of AMD according to an embodiment of the disclosure. The classification device 100 may include a processor 110, a storage medium 120, and a transceiver 130. The classification device 100 may be configured to determine the level of the AMD corresponding to a fundus image. The classification device 100 may classify the fundus image input into the classification device 100 into a first stage, a second stage, a third stage, or a fourth stage of the AMD.

The processor 110 is, for example, the central processing unit (CPU), or other programmable general-purpose or special-purpose micro control unit (MCU), microprocessor, digital signal processor (DSP), programmable controller, application specific integrated circuit (ASIC), graphics processing unit (GPU), image signal processor (ISP), image processing unit (IPU), arithmetic logic unit (ALU), complex programmable logic device (CPLD), field programmable gate array (FPGA), or other similar elements or a combination of the above elements. The processor 110 may be coupled to the storage medium 120 and the transceiver 130, and may access and execute multiple modules and various applications stored in the storage medium 120.

The storage medium 120 is, for example, any form of fixed or mobile random access memory (RAM), read-only memory (ROM), flash memory, hard disk drive (HDD), solid state drive (SSD), or similar elements or a combination of the above elements. The storage medium 120 is configured to store multiple modules or various applications that may be executed by the processor 110. In this embodiment, the storage medium 120 may store multiple models, such as a first classification model 121, a second classification model 122, and an object detection model 123.

The object detection model 123 may be configured to detect a macula in the fundus image and generate a bounding box corresponding to the macula in the fundus image. The first classification model 121 may be configured to classify the fundus image according to an image in the bounding box. In other words, the first classification model 121 classifies the fundus image according to a portion of the fundus image. The second classification model 122 may be configured to classify the fundus image according to the entire fundus image.

The transceiver 130 transmits and receives signals in a wireless or wired manner. The transceiver 130 may also perform operations such as low noise amplification, impedance matching, frequency mixing, frequency up- or down-conversion, filtering, amplification, and the like.

Figure 2:
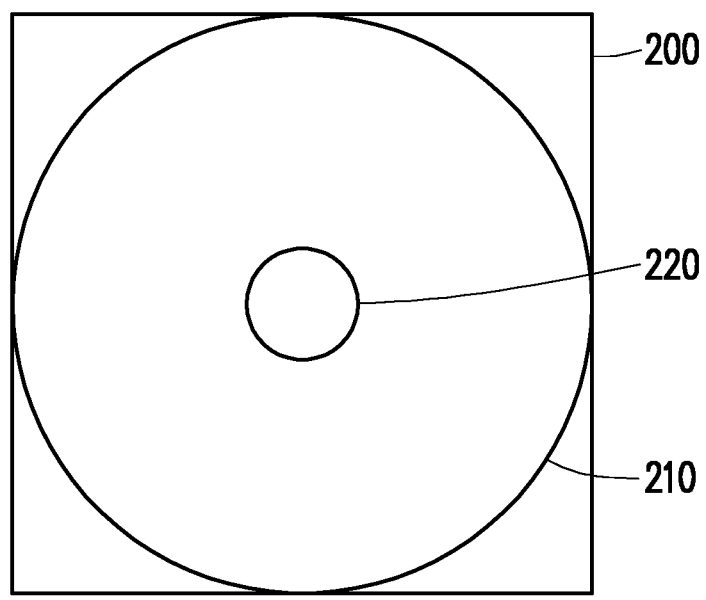
FIG. 2 is a schematic diagram showing a fundus image according to an embodiment of the disclosure.
Figure 3:
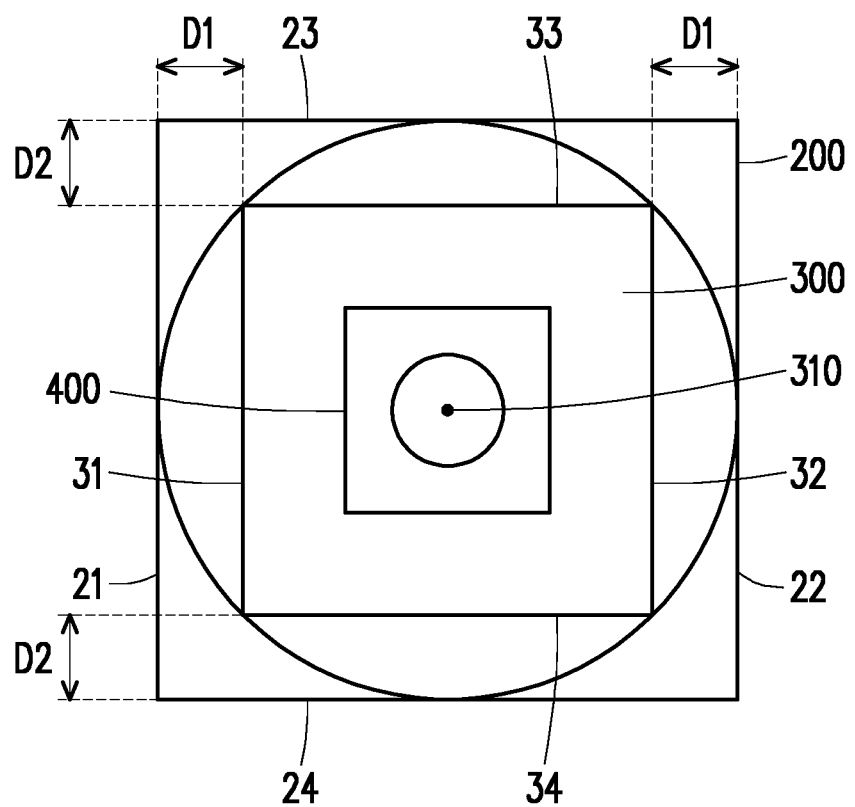
FIG. 3 is a schematic diagram showing a predetermined area and a bounding box according to an embodiment of the disclosure.

The processor 110 may obtain the fundus image through the transceiver 130. FIG. 2 is a schematic diagram showing a fundus image 200 according to an embodiment of the disclosure. The fundus image 200 may include an eyeball area 210 and a macula 220. In an embodiment, the processor 110 may extract the eyeball area 210 from the fundus image 200 according to the Hough transform. After the fundus image 200 is obtained, the processor 110 may input the fundus image 200 into the object detection model 123. The object detection model 123 is, for example, a machine learning model. The object detection model 123 may detect the macula in the fundus image 200 to generate the bounding box in the fundus image 200, as shown in FIG. 3. FIG. 3 is a schematic diagram showing a predetermined area 300 and a bounding box 400 according to an embodiment of the disclosure.

After the bounding box 400 is generated, the processor 110 may calculate an intersection over union (IOU) between the predetermined area 300 and the bounding box 400 in the fundus image 200. If the intersection over union between the predetermined area 300 and the bounding box 400 is greater than a threshold, the processor 110 may generate a classification of the fundus image 200 according to the first classification model 121. Specifically, the processor 110 may input an image in the bounding box 400 (i.e., an image of the macula 220) into the first classification model 121. The first classification model 121 may generate the classification of the fundus image 200 according to the image in the bounding box 400. The processor 110 may output the classification of the fundus image 200 through the transceiver 130 for the user's reference. The user may determine whether the fundus image 200 corresponds to the first stage, the second stage, the third stage, or the fourth stage of the AMD according to the classification output by the transceiver 130.

If the intersection over union between the predetermined area 300 and the bounding box 400 is less than or equal to the threshold, the processor 110 may generate the classification of the fundus image 200 according to the second classification model 122. Specifically, the processor 110 may input the fundus image 200 (i.e., an image of the entire eyeball) into the second classification model 122. The second classification model 122 may generate the classification of the fundus image 200 according to the fundus image 200. The processor 110 may output the classification of the fundus image 200 through the transceiver 130 for the user's reference. The user may determine whether the fundus image 200 corresponds to the first stage, the second stage, the third stage, or the fourth stage of the AMD according to the classification output by the transceiver 130.

The first classification model 121 or the second classification model 122 is, for example, a machine learning model. In an embodiment, the first classification model 121 and the second classification model 122 may have the same convolutional neural network architecture.

However, since the first classification model 121 and the second classification model 122 are trained according to different training data sets or hyperparameters, the convolutional neural network in the first classification model 121 and the convolutional neural network in the second classification model 122 may have different weights.

The fundus image 200 and the predetermined area 300 may be rectangles. The processor 110 may determine a position of the predetermined area 300 according to the geometric center of the fundus image 200. A center point 310 of the predetermined area 300 may be located at the geometric center of the fundus image 200. The fundus image 200 may have a first boundary 21, a second boundary 22, a third boundary 23, and a fourth boundary 24. The first boundary 21 and the second boundary 22 may be the short edges of the rectangle, and the third boundary 23 and the fourth boundary 24 may be the long edges of the rectangle. The second boundary 22 may be an opposite edge of the first boundary 21, and the fourth boundary 24 may be an opposite edge of the third boundary 23. On the other hand, the predetermined area 300 may have a first edge 31, a second edge 32, a third edge 33, and a fourth edge 34. The first edge 31 and the second edge 32 may be the short edges of the rectangle, and the third edge 33 and the fourth edge 34 may be the long edges of the rectangle. The second edge 32 may be an opposite edge of the first edge 31, and the fourth edge 34 may be an opposite edge of the third edge 33.

In an embodiment, the processor 110 may determine the predetermined area 300 according to the boundaries of the fundus image 200. Specifically, assuming that the predetermined area 300 is a rectangle, the storage medium 120 may pre-store a first distance D1 and a second distance D2. The processor 110 may determine that the first edge 31 of the predetermined area 300 is distanced from the first boundary 21 of the fundus image 200 by the first distance D1, and the second edge 32 of the predetermined area 300 is distanced from the second boundary 22 of the fundus image 200 by the first distance D1. On the other hand, the processor 110 may determine that the third edge 33 of the predetermined area 300 is distanced from the third boundary 23 of the fundus image 200 by the second distance D2, and the fourth edge 34 of the predetermined area 300 is distanced from the fourth boundary 24 of the fundus image 200 by the second distance D2.

In an embodiment, the processor 110 may determine the predetermined area 300 according to the diameter of the eyeball area 210. Assuming that the predetermined area 300 is a rectangle, the processor 110 may calculate a length of the long edge and a length of the short edge of the rectangle (i.e., the predetermined area 300) according to the diameter of the eyeball area 210. For example, the processor 110 may multiply the diameter of the eyeball area 210 by 0.9 to calculate the length of the long edge (i.e., the length of the third edge 33 or the fourth edge 34) of the predetermined area 300. The processor 110 may multiply the diameter of the eyeball area 210 by 0.8 to calculate the length of the short edge (i.e., the length of the first edge 31 or the second edge 32) of the predetermined area 300.

Figure 4:
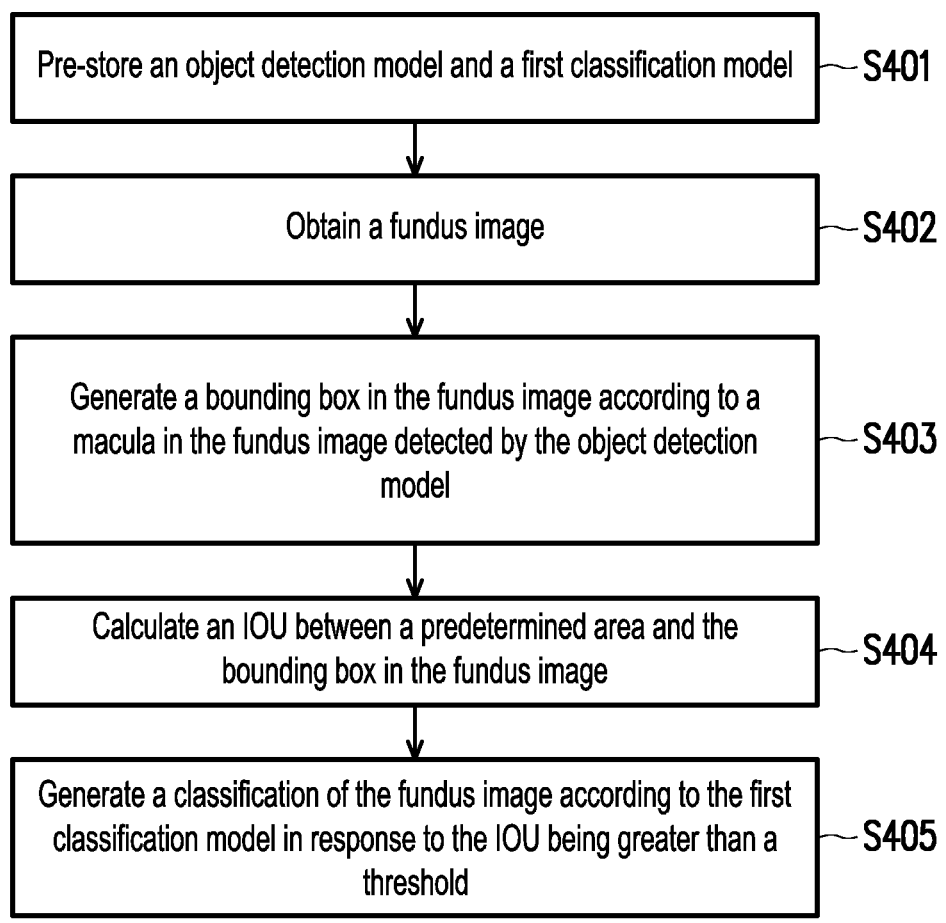
FIG. 4 is a flowchart of a classification method for classifying a level of AMD according to an embodiment of the disclosure.

FIG. 4 is a flowchart of a classification method for classifying a level of AMD according to an embodiment of the disclosure. The classification method may be implemented by the classification device 100 as shown in FIG. 1. In step S401, an object detection model and a first classification model are pre-stored. In step S402, a fundus image is obtained. In step S403, a bounding box is generated in the fundus image according to a macula in the fundus image detected by the object detection model. In step S404, an intersection over union between a predetermined area and the bounding box in the fundus image is calculated. In step S405, a classification of the fundus image is generated according to the first classification model in response to the intersection over union being greater than a threshold.

In summary of the foregoing, the classification device of the disclosure may store the first classification model and the second classification model. The first classification model may determine the level of the AMD according to the bounding box in the fundus image, and the second classification model may determine the level of the AMD according to the entire fundus image. If the object detection model determines that the macula is present in the predetermined area in the fundus image, it means that the position of the macula in the fundus image is reasonable. Accordingly, the classification device may classify the fundus image according to the first classification model. If the object detection model determines that the macula is not present in the predetermined area in the fundus image, it means that the position of the macula in the fundus image is not reasonable. Accordingly, the classification device may classify the fundus image according to the second classification model. In other words, if the position of the macula in the fundus image is reasonable, the classification device may classify the level of the AMD according to the same criteria with the doctor.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. An eye examining device for classifying a level of age-related macular degeneration, the eye examining device comprising:
   a transceiver;
   a camera;
   a storage medium, storing an object detection model, a first classification model, and a second classification model different from the first classification model; and
   a processor, coupled to the camera, the storage medium and the transceiver, wherein the processor is configured to:
   capture a fundus image through the camera;
   generate a bounding box in the fundus image according to a macula in the fundus image detected by the object detection model;
   calculate an intersection over union between a predetermined area and the bounding box in the fundus image, wherein the fundus image and the predetermined area are rectangles, a center point of the predetermined area is located at a geometric center of the fundus image, a first edge of the predetermined area is distanced from a first boundary of the fundus image by a first distance, and a second edge of the predetermined area is distanced from a second boundary of the fundus image by the first distance, wherein the second edge is an opposite edge of the first edge, and the second boundary is an opposite boundary of the first boundary;
   input an image in the bounding box into the first classification model to generate a classification of the fundus image in response to the intersection over union being greater than a threshold, wherein the first classification model was trained by a portion of fundus image;
   input the fundus image into the second classification model to generate the classification in response to the intersection over union being less than or equal to the threshold, wherein the second classification model was trained by an entire fundus image; and
   output the classification through the transceiver, wherein the classification indicates one of a first stage, a second stage, a third stage, and a fourth stage of the age-related macular degeneration.

2. The eye examining device described in claim 1, wherein the predetermined area is a first rectangle, and the processor is further configured to:
   obtain an eyeball area in the fundus image; and
   generate a length of a long edge and a length of a short edge of the first rectangle according to a diameter of the eyeball area.

3. The eye examining device described in claim 1, wherein the first classification model and the second classification model have a same convolutional neural network architecture.

4. An eye examining method for classifying a level of age-related macular degeneration, the eye examining method comprising:

pre-storing an object detection model, a first classification model, and a second classification model different from the first classification model;

capturing a fundus image through a camera;

generating a bounding box in the fundus image according to a macula in the fundus image detected by the object detection model;

calculating an intersection over union between a predetermined area and the bounding box in the fundus image, wherein the fundus image and the predetermined area are rectangles, a center point of the predetermined area is located at a geometric center of the fundus image, a first edge of the predetermined area is distanced from a first boundary of the fundus image by a first distance, and a second edge of the predetermined area is distanced from a second boundary of the fundus image by the first distance, wherein the second edge is an opposite edge of the first edge, and the second boundary is an opposite boundary of the first boundary;

inputting an image in the bounding box into the first classification model to generate a classification of the fundus image in response to the intersection over union being greater than a threshold, wherein the first classification model was trained by a portion of fundus image;

inputting the fundus image into the second classification model to generate the classification in response to the intersection over union being less than or equal to the threshold, wherein the second classification model was trained by an entire fundus image; and outputting the classification, wherein the classification indicates one of a first stage, a second stage, a third stage, and a fourth stage of the age-related macular degeneration.

* * * * *